United States Patent
Leach et al.

(10) Patent No.: US 7,462,265 B2
(45) Date of Patent: Dec. 9, 2008

(54) REDUCED VOLUME ELECTROCHEMICAL SENSOR

(75) Inventors: Christopher Philip Leach, Inverness (GB); Erica Mary Beck, Nairn (GB)

(73) Assignee: Lifescan, Inc., Milpitas, CA (US)

( * ) Notice: Subject to any disclaimer, the term of this patent is extended or adjusted under 35 U.S.C. 154(b) by 734 days.

(21) Appl. No.: 10/860,220

(22) Filed: Jun. 2, 2004

(65) Prior Publication Data

US 2005/0023136 A1 Feb. 3, 2005

Related U.S. Application Data

(60) Provisional application No. 60/476,734, filed on Jun. 6, 2003.

(51) Int. Cl.
*G01N 27/327* (2006.01)

(52) U.S. Cl. .............. 204/403.14; 204/403.01; 204/403.11

(58) Field of Classification Search .................. 204/403.01–403.04
See application file for complete search history.

(56) References Cited

U.S. PATENT DOCUMENTS

| | | | |
|---|---|---|---|
| 5,653,918 A | 8/1997 | Towlson | |
| 6,258,229 B1 | 7/2001 | Winarta et al. | |
| 6,284,125 B1 | 9/2001 | Hodges et al. | |
| 6,287,451 B1 | 9/2001 | Winarta et al. | |
| 6,302,855 B1 | 10/2001 | Lav et al. | |
| 6,447,657 B1 | 9/2002 | Bhullar et al. | |
| 6,558,528 B1 * | 5/2003 | Matzinger | 205/777.5 |
| 6,719,923 B2 | 4/2004 | Stiene et al. | |
| 6,733,655 B1 | 5/2004 | Davies et al. | |
| 2002/0092612 A1 | 7/2002 | Davies et al. | |
| 2003/0217918 A1 | 11/2003 | Davies et al. | |

FOREIGN PATENT DOCUMENTS

| | | |
|---|---|---|
| EP | 0359831 A1 | 3/1990 |
| EP | 0505494 B1 | 9/1992 |
| EP | 0685737 B1 | 12/1995 |
| WO | WO 01/67099 A1 | 9/2001 |
| WO | WO 01/73124 A2 | 10/2001 |
| WO | WO 01/75438 A2 | 10/2001 |
| WO | WO 0232559 A1 * | 4/2002 |

* cited by examiner

*Primary Examiner*—Alex Noguerola

(57) ABSTRACT

An electrochemical glucose sensor comprising a base substrate, a conductive layer disposed on said base substrate, where said conductive layer comprises a reference electrode and at least two working electrodes; an insulation layer disposed on a part of said conductive layer, a reagent layer disposed on said working electrodes and on at least a part of said reference electrode, an adhesive layer disposed on a portion of said reagent layer and conductive layer wherein said adhesive layer substantially defines an area of said reference electrode which can be wetted by a liquid sample and said insulation layer substantially defines an area of said working electrodes which can be wetted by a liquid sample.

9 Claims, 6 Drawing Sheets

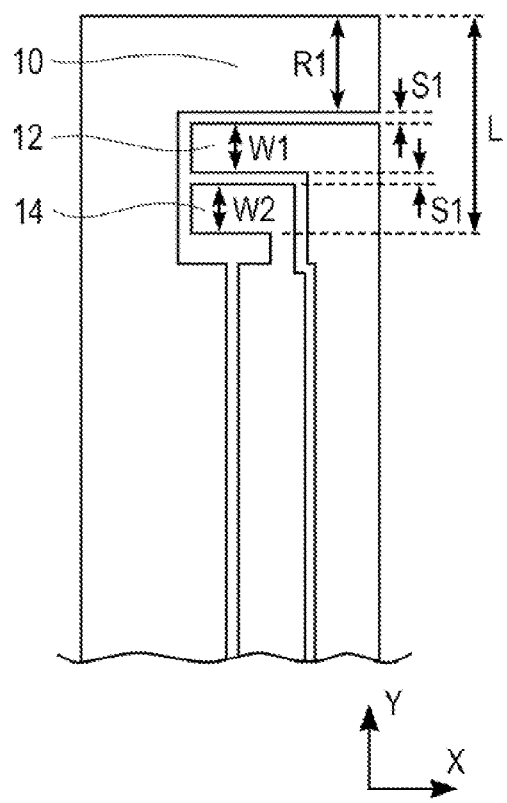
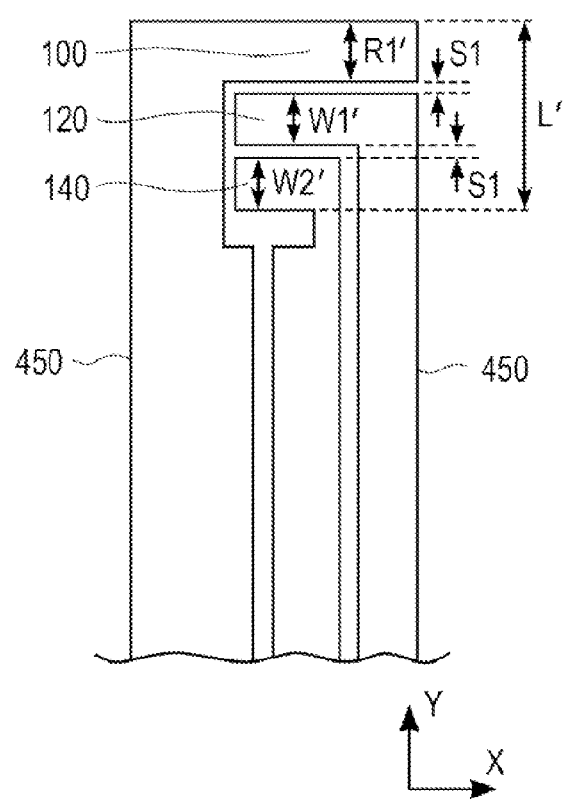
FIG. 2A
PRIOR ART
FIG. 2B

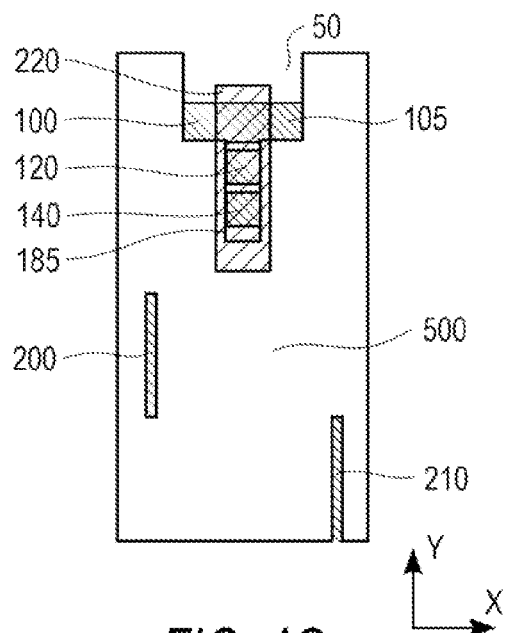
FIG. 4C
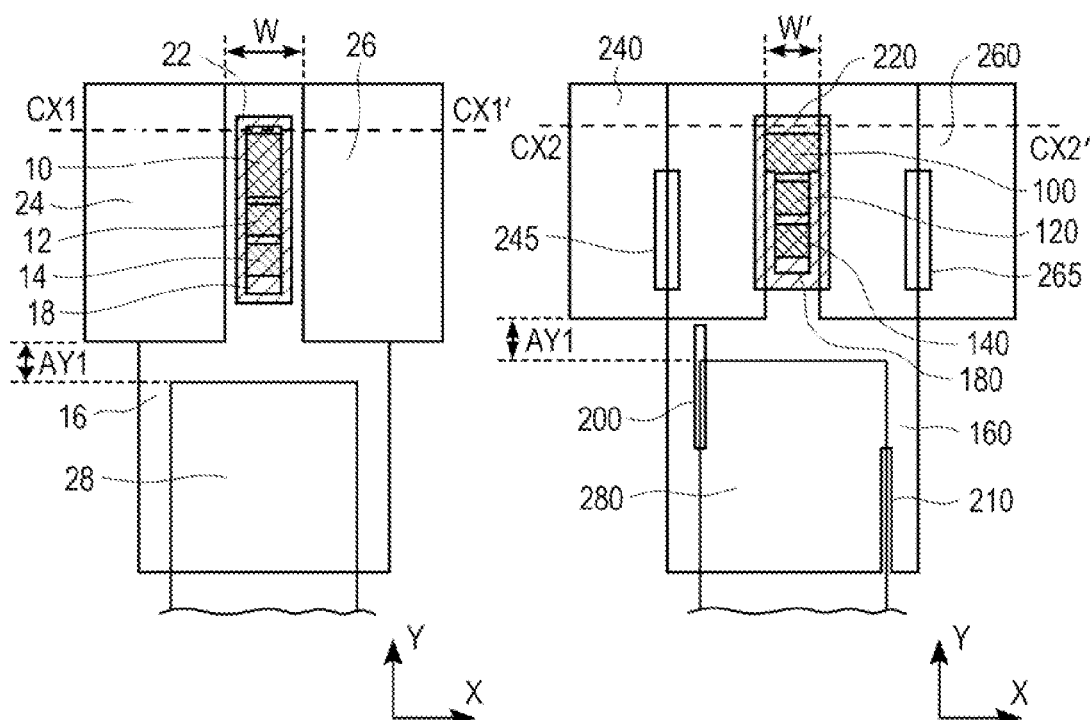
FIG. 5A
PRIOR ART
FIG. 5B

US 7,462,265 B2

REDUCED VOLUME ELECTROCHEMICAL SENSOR

CROSS-REFERENCE

This application claims the benefit of U.S. Provisional Application No. 60/476,734 filed Jun. 6, 2003, which application is incorporated herein by reference.

BACKGROUND OF THE INVENTION

Field of the Invention

The present invention relates, in general, to electrochemical strips for the detection of glucose and, more particularly, to electrochemical strips for the detection of glucose wherein the insulation layer incorporated a T-shaped aperture.

The detection of the concentration of glucose in blood may be accomplished using electrochemical meters and associated test strips such as the Ultra meter and Ultra test strip, which are available from LifeScan, Inc. When utilizing such electrochemical meters and test strips, a patient would normally lance the skin to draw blood into the strip. The amount of blood required is a function of a number of factors, including the shape and size of the sample cell on the strip. The amount of blood required to fill the sample chamber is important because the user may perceive that large blood samples will require larger lancing wounds and, thus, more pain. It would, therefore, be advantageous to design test strips with small sample chambers.

SUMMARY OF THE INVENTION

In an embodiment of this invention, a sensor may comprise a base substrate, a conductive layer disposed on the substrate, an insulation layer disposed on a part of the conductive layer and exposing a portion of the conductive layer, a reagent layer covering at least a portion of the exposed conductive layer, an adhesive layer touching, for example, overlapping or lying adjacent to the reagent layer and the conductive layer, and a hydrophilic layer disposed on top of the adhesive to form a sample receiving chamber. In a reduced volume strip embodiment of the present invention, the insulation layer incorporated a T-shaped aperture that enabled a reduction in the sample receiving chamber by increasing the width and decreasing the length of the reference electrode. In the reduced volume strip embodiment, the reference electrode has its width defined by the walls of the sample receiving chamber by an adhesive layer, whereas the working electrodes have their width defined by the insulation layer. By decreasing the size of the sample chamber width, this caused the reagent layer to touch or overlap with the adhesive layer. The unique architecture of the reduced volume sample receiving chamber allows for a reduction of its width and length.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 2A and 2B are a top view of a conductive layer of a respective test strip embodiment of the prior art and a reduced volume embodiment of the present invention.

FIG. 4C is a simplified partial top view of a reagent layer disposed on the conductive layer and insulation layer of an alternative test strip embodiment of the present invention.

FIGS. 5A and 5B are a simplified partial top view of an adhesive layer disposed on the insulation layer and reagent layer of a respective test strip embodiment of the prior art and a reduced volume embodiment of the present invention.

DETAILED DESCRIPTION OF ILLUSTRATIVE EMBODIMENTS OF THE INVENTION

Figure 1A:
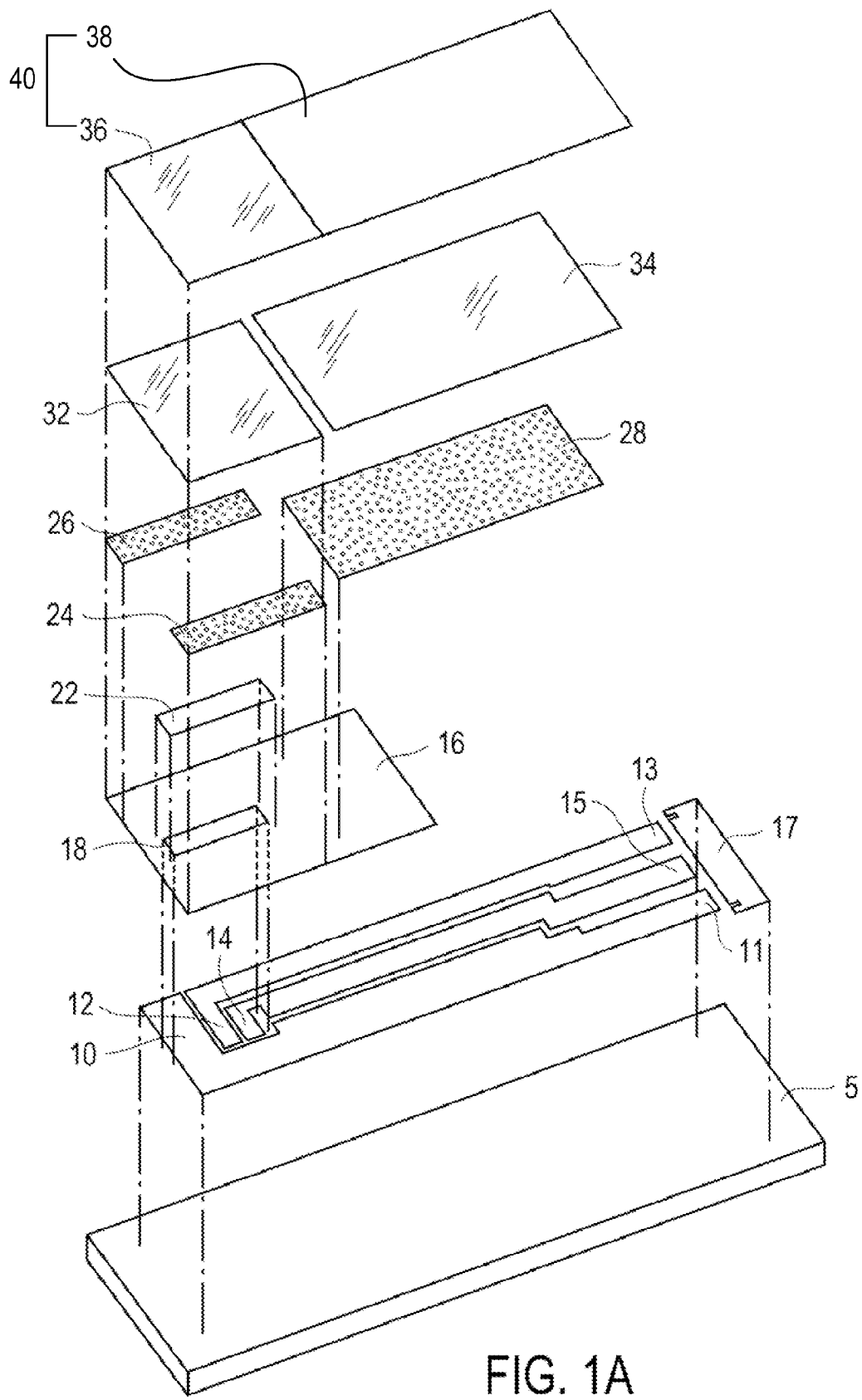
FIGS. 1A and 1B are an exploded perspective view of a respective test strip embodiment of the prior art and a reduced volume embodiment of the present invention.
Figure 1B:
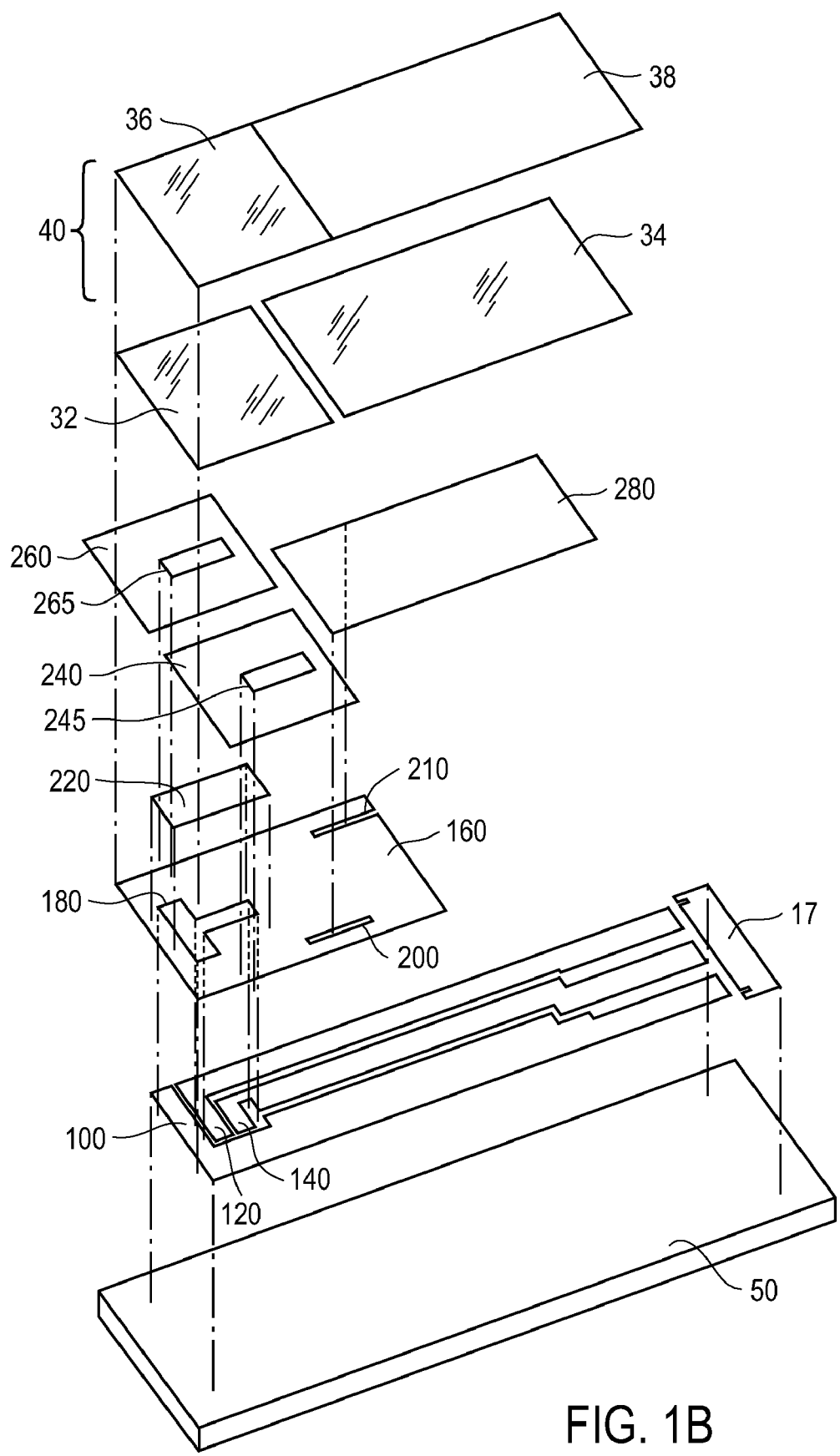

FIGS. 1A and 1B are an exploded perspective view of a respective test strip embodiment of the prior art and a reduced volume embodiment of the present invention. The prior art test strip of FIG. 1A includes a base substrate 5, a first working electrode 12, a second working electrode 14, a reference working electrode 10, a first contact 13, a second contact 15, a reference contact 11, a strip detection bar 17, an insulation layer 16 having a cutout 18, an reagent layer 22, a first adhesive pad 24, a second adhesive pad 26, a third adhesive pad 28, a proximal hydrophilic film 32, a distal hydrophilic film 34, and a top film 40 having a clear portion 36 and an opaque portion 38. The reduced volume test strip of FIG. 1B includes a base substrate 50, a first working electrode 120, a second working electrode 140, a reference working electrode 100, a strip detection bar 17, an insulation layer 160 having a T-shaped aperture 180, a first insulation registration guide 200, a second insulation registration guide 210, an reagent layer 220, a first adhesive pad 240, a second adhesive pad 260, a third adhesive pad 280, a first singulation guide 245, a second singulation guide 265, a first a proximal hydrophilic film 32, a distal hydrophilic film 34, and a top layer which includes a clear portion 36 and an opaque portion 38.

A test strip according to the prior art and present invention is manufactured in a series of steps wherein the elements as illustrated in FIGS. 1A and 1B are deposited on base substrate (5 or 50) using, for example, a screen printing process. In an embodiment of the prior art and present invention, base substrate (5 or 50) is an electrically insulating material such as plastic, glass, ceramic, and the like. In a preferred embodiment of this invention, base substrate (5 or 50) may be a plastic such as, for example, nylon, polycarbonate, polyimide, polyvinylchloride, polyethylene, polypropylene, PETG, or polyester. More particularly the polyester may be, for example Melinex® ST328 which is manufactured by DuPont Teijin Films. Substrate (5 or 50) may also include an acrylic coating which is applied to one or both sides to improve ink adhesion.

The first layer deposited on base substrate (5 or 50) is the conductive layer for the respective prior art embodiment and the reduced volume embodiment. FIGS. 2A and 2B shows a top view of a conductive layer of a respective test strip embodiment and reduced volume test strip embodiment of the present invention. In FIG. 2A, the conductive layer includes reference electrode 10, first working electrode 12, and second working electrode 14. First and second working electrodes (12 and 14) have a respective length W1 and W2 which may both be, for example, about 0.8 mm. Reference electrode 10 may have a length R1 which may be, for example, about 1.6 mm. A distance between reference electrode 10 and first working electrode 12; or between first working electrode 12 and second working electrode 14 may be denoted as electrode spacing S1. As a non-limiting example, electrode spacing S1 may be about 0.2 mm. A total distance spanned by all three electrodes may be denoted as the sample receiving chamber length L. As a non-limiting example, the sample receiving chamber length L may be about 3.2 mm.

In an embodiment of the present invention that reduces the sample receiving chamber volume, the conductive layer may also include a reference electrode 100, first working electrode 120, and second working electrode 140 as illustrated in FIG. 2B. First and second working electrodes (120 or 140) have a length W1' and W2' which may both be, for example, about 0.9 mm. Reference electrode 100 may have a length R1' which may be, for example, about 1 mm. A distance between reference electrode 10 and first working electrode 12; or between first working electrode 12 and second working electrode 14 may be denoted as electrode spacing S1. As a non-limiting example, electrode spacing S1 may be about 0.2 mm. A total distance spanned by all three electrodes may be denoted as the sample receiving chamber length L'. As a non-limiting example, the sample receiving chamber length L' may be about 3.1 mm. It should be noted that changing the conductive layer geometry as shown in FIG. 2B, enabled the sample chamber length L' to be reduced to 3.1 mm from the 3.6 millimeter sample chamber length L representing a 14% decrease.

Figure 3A:
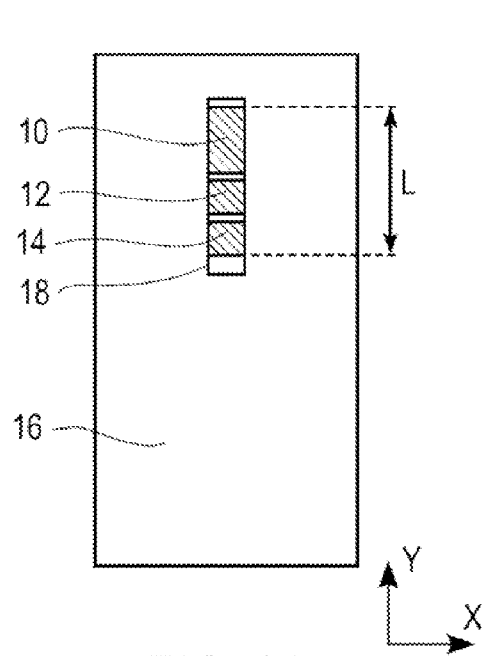
FIGS. 3A and 3B are a simplified partial top view of an insulation layer disposed on the conductive layer of a respective test strip embodiment of the prior art and a reduced volume embodiment of the present invention.
Figure 3B:
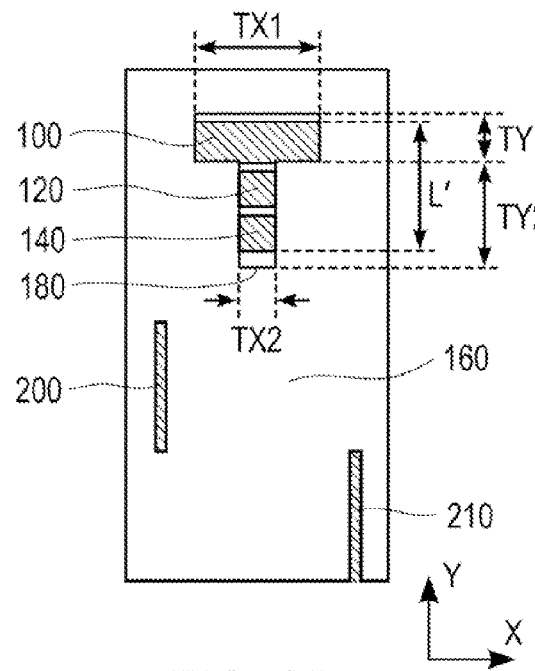

The second layer deposited on base substrate (5 or 50) is the insulation layer for the respective prior art embodiment and the reduced volume embodiment. FIGS. 3A and 3B shows a simplified partial top view of an insulation layer disposed on the conductive layer of a respective prior art test strip embodiment and reduced volume test strip embodiment of the present invention. As a non-limiting example, insulation layer (16 or 160) may be Ercon E6110-116 Jet Black Insulayer Ink which may be purchased from Ercon, Inc. In FIG. 3A, insulation layer 16 further includes a cutout 18 which exposes a portion of reference electrode 10, first working electrode 12, and second working electrode 14 which can be wetted by a liquid sample. It should be noted that only the area of the electrode which is exposed to a liquid sample can exchange electrons with an electrochemical species and that the exposed area is directly proportional to the magnitude of the measured current in response to an applied voltage. As a non-limiting example, cutout 18 may be a rectangle having a width along the X-axis of about 0.7 mm and a length along the Y-axis of about 4.1 mm. In an embodiment of the prior art invention, first and second working electrodes (12 and 14) may have an area of about 0.6 mm² and reference electrode 10 may have an area of about 1.2 mm². In certain situations where the current at first or second working electrode (12 or 14) is sufficiently large, it may be desirable for the area of reference electrode 10 to be about twice as big as the area of either first or second working electrode (12 and 14) so that the current at reference electrode (10) does not limit the amount of current measured at either first or second working electrode (12 or 14).

In a reduced volume embodiment of the present invention that reduces the sample receiving chamber volume, insulation layer 160 may have a T-shaped aperture 180 as shown in FIG. 3B which exposes a portion of reference electrode 100, first working electrode 120, and second working electrode 140. T-shaped aperture 180 may be described as 2 juxtaposed rectangles which may further include a distal rectangle which substantially overlaps with reference electrode 100 and a proximal rectangle which substantially overlaps with first and second working electrodes (120 and 140). As a non-limiting example, the distal rectangle may have a distal T-width TX1 which may be about 2.5 mm and a distal T-length TY1 which may be about 1.1 mm as illustrated in FIG. 3B. The proximal rectangle may have a proximal T-width TX2 which may be about 0.7 mm and a proximal T-length TY2 which may be about 2.5 mm as illustrated in FIG. 3B. It should be noted that T-shaped aperture 180 causes reference electrode 100 to increase in width (along the X-axis) and decrease in length (along the Y-axis). This allows the sample volume to decrease while maintaining a reference:/working electrode area ratio of about 2:1.

Insulation layer 160 further includes a first and second insulation registration guides (200 and 210) as illustrated in FIG. 3B. As a non-limiting example, first and second insulation registration guide (200 and 210) may be a rectangle having a width along the X-axis of about 0.2 mm and a length along the Y-axis of about 2.9 mm. In an embodiment of the present invention, first and second insulation registration guides (200 and 210) may be used to align the printing of insulation layer 160 with respect to the conductive layer. The rectangular aperture within first and second insulation registration guides (200 and 210) should be completely filled with the conductive layer such that no portion of insulation layer 160 is exposed therefrom. This indicates an acceptable alignment of insulation layer 160 to the conductive layer. In an embodiment of the invention, an ideal alignment may include having both first and second insulation registration guides (200 and 210) located about 0.3 mm from a side edge 450 of the conductive layer (see FIG. 2B). A manual or automated alignment system may be used to confirm that insulation layer 160 is properly aligned with the conductive layer. As a non-limiting example, an automated alignment system may further includes a means for capturing a visual image of first and second insulation registration guides (200 and 210) coupled to a feedback loop to enable a positional change in the insulation print mechanism to improve the alignment between the respective layers.

Figure 4A:
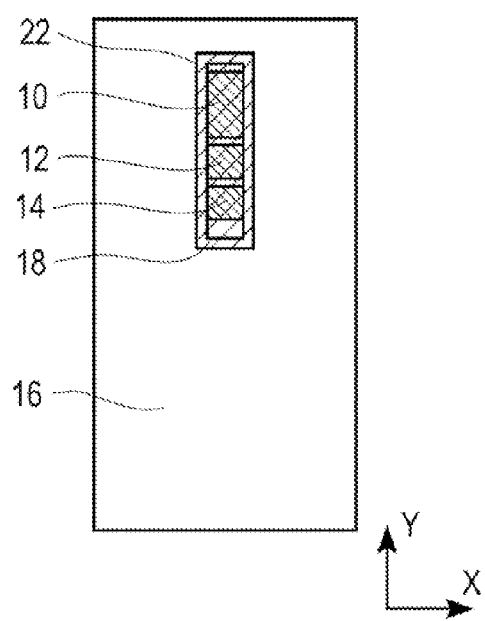
FIGS. 4A and 4B are a simplified partial top view of a reagent layer disposed on the conductive layer and insulation layer of a respective test strip embodiment of the prior art and a reduced volume embodiment of the present invention.
Figure 4B:
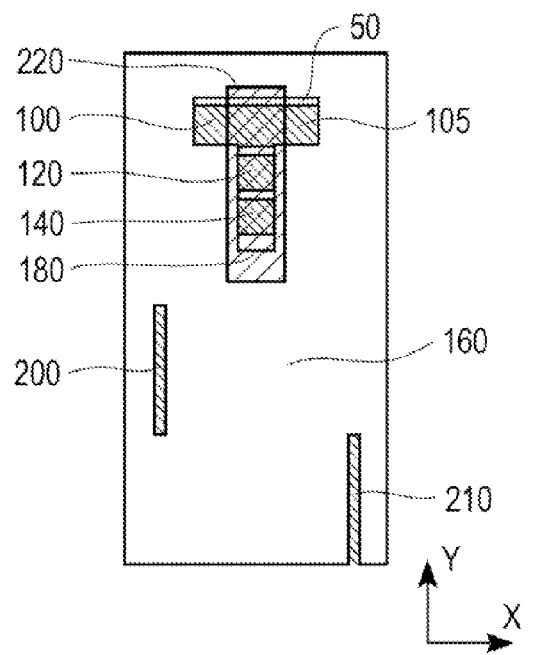

The third layer deposited on base substrate (5 or 50) is a reagent layer (22 or 220) for the respective prior art embodiment and the reduced volume embodiment. FIGS. 4A and 4B shows a simplified partial top view of a reagent layer disposed on the conductive layer and insulation layer of a respective prior art test strip embodiment and reduced volume test strip embodiment of the present invention. For FIG. 4A, reagent layer 22 which may incorporates chemicals, proteins, enzymes, buffers, anti-bodies, coagulating factors and the like is disposed within and nearby to cutout 18. In FIG. 4A, reagent layer 22 is a rectangle which is disposed over the entire cutout 18 and a portion of insulation layer 16. In an embodiment of this invention, reagent layer 22 may have a width (along the X-axis) of about 1.3 mm and a length (along the Y-axis) of about 4.7 mm which are greater than the respective width and length of cutout 18 such that it accounts for routine positional variations in the manufacturing process. This ensures that all electrodes (10, 12, and 14) are entirely coated with reagent layer 22 within the desired frequency. In an embodiment of this invention, reagent layer 22 may be disposed using a screen printing process. Additionally, reagent layer 22 may be formed by 2 consecutive screen printing cycles to minimize the frequency of pinholes.

In a reduced volume embodiment of the present invention that reduces the sample receiving chamber volume, reagent layer 220 is disposed on at least a portion of the electrodes (100, 120, and 140) and insulation layer 160. The composition of reagent layer 220 may be similar to reagent layer 22. Other examples of possible reagent formulations or inks for which may be used in the present invention can be found in U.S. Pat. Nos. 5,708,247 and 6,046,051; published international applications WO01/67099 and WO01/73124, all of which are incorporated by reference herein. In FIG. 4B, reagent layer 220 is a rectangle which is disposed over first and second working electrode (120 and 140) and a portion of reference electrode 100. In contrast to FIG. 4A, reagent layer 220 does not cover the entire T-shaped aperture 180 as illustrated in FIG. 4B. In an embodiment of this invention, reagent layer 220 may have a width (along the X-axis) of about 1.3 mm and a length (along the Y-axis) of about 4.2 mm which are greater than the respective proximal T-width TX2 and the length of T-shaped aperture 180 such that it accounts for routine positional variations in the manufacturing process. This ensures that first and second working electrodes (120 and 140) are entirely coated with reagent layer 220 within the desired frequency. In contrast to FIG. 4A, reagent layer 220 does not cover all of reference electrode 100 which is exposed by T-shaped aperture 180 as shown by uncoated area 105. In another embodiment of this invention, the width of reagent layer 220 may be increased to coat in its entirety reference electrode 100, first working electrode 120, and second working electrode 140. In an embodiment of this invention, reagent layer 220 may be disposed using a screen printing process. Additionally, reagent layer 220 may be formed by 2 consecutive screen printing cycles to minimize the frequency of pinholes.

In an alternative embodiment of the present invention that reduces the sample receiving chamber volume, reagent layer 220 is disposed on at least a portion of the electrodes (100, 120, and 140) and insulation layer 500. The composition of reagent layer 220 may be similar to reagent layer 22. In FIG. 4C, insulation layer 500 further includes an open T-shaped aperture 185. In contrast to FIG. 4C, T-shaped aperture 180 as illustrated in FIG. 4B has a closed structure wherein a majority portion of each side of reagent layer 220 touches insulation layer 160. It was subsequently found that the reagent layer adheres more strongly to the insulation layer when a majority portion of each side of reagent layer 220 touches the insulation layer. In FIG. 4C, a side of reagent layer 220 which is located on the proximal end of the sensor strip does not touch the insulation layer because of the geometry of open T-shaped aperture 185. It was found that strips prepared in this manner as shown in FIG. 4C resulted in having reagent layer 220 flake off the strip. It has been theorized that the insulation layer is more hydrophilic than base substrate 50 which may be a polyester and that more hydrophilic surfaces help anchor reagent to a surface and prevent flaking. Because the flaking process is most likely initiated at the edges of the reagent layer, the hydrophilicity of the surface immediately underneath the edge of the reagent layer is the most critical. Therefore, a preferred embodiment of this invention is to use T-shaped aperture 180 which is closed as opposed to open T-shaped aperture 185 when the base substrate comprises polyester and the insulation layer comprises Ercon E6110-116 Jet Black Insulayer Ink.

The fourth layer deposited on base substrate (5 or 50) is an adhesive layer for the respective prior art embodiment and the reduced volume embodiment. FIGS. 5A and 5B shows a simplified partial top view of an adhesive layer disposed on the insulation layer and reagent layer of a respective test strip embodiment and reduced volume test strip embodiment of the present invention. In FIG. 5A adhesive layer further includes first, second, and third adhesive pads (24, 26, and 28). First and second adhesive pads (24 and 26) may be a rectangular shape having a width along the X-axis of about 3.5 mm and a length along the Y-axis of about 6.3 mm. First and second adhesive pads (24 and 26) both have a side edge which is located adjacent to reagent layer 22. The distance between the side edges located closest to reagent layer 22 represents a sample receiving chamber width W as illustrated in FIG. 5A. As a non-limiting example, sample receiving chamber width W may be about 1.9 mm. The side edges of first and second adhesive pads (24 and 26) located adjacent to reagent layer 22 each defining a wall of the sample receiving chamber. It should be noted that reagent layer 22 does not touch or overlap with first or second adhesive pad (24 and 26) because the sample receiving chamber width W is greater than the width of reagent layer 22. Third adhesive pad 28 comprises a rectangular shape having a width along the X-axis of about 3.9 mm and a length along the Y-axis of about 13 mm. FIG. 5A illustrates that third adhesive pad 28 is located near second working electrode 14 and is positioned such that an adhesive spacing AY1 is about 1 mm.

In an improved embodiment of the present invention that reduces the sample receiving chamber volume, an adhesive layer further includes first, second, and third adhesive pads (240, 260, and 280). In contrast to the strip in FIG. 5A, first and second adhesive pads (240 and 260) are moved closer together to form a sample receiving chamber width W' that is smaller than sample receiving chamber width W which reduces the volume of the sample receiving chamber. As a non-limiting example, sample receiving chamber width W' may be about 1.3 mm which reduces the sample receiving chamber width by about 32% compared to FIG. 5A. In this arrangement, a portion of the adhesive layer overlaps with reagent layer 220. First and second adhesive pads (240 and 260) have a rectangular shape having a width along the X-axis of about 4.2 mm and a length along the Y-axis of about 5.8 mm. First and second adhesive pads (240 and 260) both further include a side edge which is located closest to reagent layer 220. The distance between the side edges located closest to reagent layer 220 represents a sample receiving chamber width W' as illustrated in FIG. 5B. The side edges of first and second adhesive pads (240 and 260) located closest to reagent layer 220 each defining a wall of the sample receiving chamber. It should be noted that reagent layer 220 touches or overlaps with first or second adhesive pad (240 and 260) because the sample receiving chamber width W' is smaller than the width of reagent layer 220. In an embodiment of the present invention, the adhesive layer may comprise a water based acrylic copolymer pressure sensitive adhesive which is commercially available from Tape Specialties LTD in Tring, Herts, United Kingdom (part#A6435). Third adhesive pad 280 comprises a rectangular shape having a width along the X-axis of about 3.9 mm and a length along the Y-axis of about 13 mm. Third adhesive pad 280 is located near second working electrode 140 and is positioned such that the adhesive spacing AY1 as illustrated in FIG. 5B is about 1 mm.

In an embodiment of the present invention, the adhesive layer comprising three adhesive pads (240, 260, and 280) may be simultaneously stencil printed to insulation layer 160, reagent layer 220, and electrodes (100, 120, and 140). In order to accurately and precisely align all three adhesive pads (240, 260, and 280), visual alignment may be performed using first and second insulation registration guides (200 and 210). An alignment of the adhesive stencil print system may align the side edges of third adhesive pad 280 with the midpoint (along the X-axis) of the rectangles within first and second insulation registration guides (200 and 210) as shown in FIG. 5B. An automated alignment system may include a means for capturing a visual image of third adhesive pad 280 relative to the insulation registration guides (200 and 210) coupled to a feedback system enabling a positional change of the print mechanism to improve registration of the adhesive layer to insulation layer 160.

First and second adhesive pads (240 and 260) includes a respective first and second singulation guide (245 and 265) which may also be used to align the adhesive pads (240 and 260) with the side edges of insulation layer 160 as shown in FIG. 5B. First and second singulation guides (245 and 265) may also be used as a registration mark for singulating a test strip by a slicing process. First and second singulation guides (245 and 265) may be a rectangle located within first and second adhesive pads (240 and 260), wherein the rectangle has a width (along the X-axis) of about 0.7 mm and a length (along the Y-axis) of about 2.8 mm. When slicing test strips using a tacky adhesive, it is common for adhesive residue to build up on the slicing blades. This can cause strips to adhere to the blade which in turn causes throughput issues in packaging. In addition, adhesive residue build up can cause strips to be sliced with poor edge definition where the edges of the strip become distorted and non-perpendicular. This can also cause delamination and shifting of laminate layers with respect to each other. In order to prevent significant adhesive build up, the slicing machine may be periodically cleaned after slicing a particular number of strips. This cleaning step is exceedingly undesirable because it stops the manufacturing line and is also a potentially dangerous step where operator injury can occur. One of the objectives of the present invention is to reduce the frequency of the cleaning cycles by reducing the amount of adhesive that is exposed to the blade. By using first and second singulation guides (245 and 265), the strip reduces the amount of sliced adhesive by about 50%, and thus, improves the strip slicing throughput by decreasing the cleaning cycle frequency. It should also be noted that the width of third adhesive pad 280 is less than the width of insulation layer 160 such that no portion of third adhesive pad 280 touches the slicing blade.

In FIG. 5B, first and second adhesive pad exposes a portion of reference electrode 100 which may be wetted by a liquid sample. This is in contrast to the case in which insulation layer 160 exposes a portion of first and second working electrode (120 and 140) which may be wetted by a liquid sample. By using the adhesive layer to expose the portion of reference electrode 100, this allowed the reference electrode width to be increased and be coincident with sample chamber width W'. In turn, using a wider reference electrode 100 allowed the length of reference electrode to decrease while maintaining a similar reference electrode area as in FIG. 5A. The strategy of defining reference electrode area with adhesive allows a more efficient use of sample chamber area allowing its length to be reduced and an overall reduction in sample chamber volume while maintaining a reference:working electrode area of about 2:1

The test strip of the present invention may have a portion of reagent layer 220 in physical contact with the adhesive layer as illustrated in FIG. 5B. Previously, it was believed that reagent layer 220 should not be in physical contact with the adhesive layer because chemicals in the adhesive can migrate into reagent layer 220 and react with the enzyme and/or redox mediators causing stability problems. In particular, it was unexpected that the use of water based adhesives could be used in the test strip because moisture may lead to the instability of the redox mediator and redox enzyme. In addition, it was not anticipated that having the adhesive layer overlapping reagent layer 220 could form a liquid impermeable barrier to form the walls of the sample receiving chamber allowing a relatively constant sample receiving chamber volume to be maintained during the measurement. Initially, it was believed that reagent layer 220 would solubilize underneath the adhesive layer causing the volume of the sample receiving chamber to change with time. Such a change in chamber volume, if sufficiently large enough, may also degrade the accuracy of the glucose concentration output. The sample receiving chamber should be designed to have a relatively constant volume over the duration of the test such that if does not affect the glucose output. It is now believed that the use of a water based adhesive helps improve the liquid impermeable barrier within the sample receiving chamber and does not cause any instability to the reagent layer. Because the adhesive contains a significant amount of water such as, for example, 50% by weight, the adhesive initially causes reagent layer 220 to partially dissolve allowing the acrylic copolymer to stick strongly to either base substrate 50 and/or insulation layer 160 such that it is sufficient to bind the layers together and define a sufficiently stable sample receiving chamber volume for at least 5 seconds.

In another embodiment of the reduced volume strip, reagent layer 220 can be have the same width as the sample receiving chamber W'. Under ideal manufacturing conditions, the side edges (parallel to the Y-axis) of reagent layer 220 will be immediately adjacent to first and second adhesive pads (240 and 260). However, during routine manufacturing there will be some positional variation in disposing first and second adhesive pads along the X-axis direction causing one of the side edges to overlap with a portion of the adhesive layer. However, by targeting the reagent layer 220 to have a width the same as sample receiving chamber width W'. This will minimize the amount of reagent layer 220 immediately underneath the adhesive layer.

The fifth layer deposited on base substrate (5 or 50) is a hydrophilic layer for the respective prior art embodiment and the reduced volume embodiment. A hydrophilic film further includes a distal hydrophilic film 32 and proximal hydrophilic film 34 for both the prior art and present invention. Proximal hydrophilic film 32 is disposed over and substantially overlaps first and second adhesive pads (24 and 26, or 240 and 260) to form a roof portion of the sample receiving chamber. Similarly, distal hydrophilic film 34 substantially overlaps third adhesive pads (28 or 280). As a non-limiting example, distal and proximal hydrophilic films (32 and 34) may be a PET having one hydrophilic surface such as anti-fog coated PET which is commercially available from 3M. It should be noted that both distal and proximal hydrophilic films (32 and 34) are visibly transparent enabling a user to observe a liquid sample filling the sample receiving chamber.

The sixth layer deposited on base substrate (5 or 50) is a top layer 40 for the respective prior art embodiment and the reduced volume embodiment. A top layer 40, which further includes a clear portion 36 and opaque portion 38, is disposed on and adhered to the hydrophilic films. As a non-limiting example, top layer 40 may be a PET. It should be noted that the clear portion 36 substantially overlaps proximal hydrophilic film 32 which allows a user to visually confirm that the sample receiving chamber is sufficiently filled. Opaque portion 38 helps the user observe a high degree of contrast between a colored fluid such as, for example, blood within the sample receiving chamber and the opaque section of the top film.

Figures 6A, 6B:
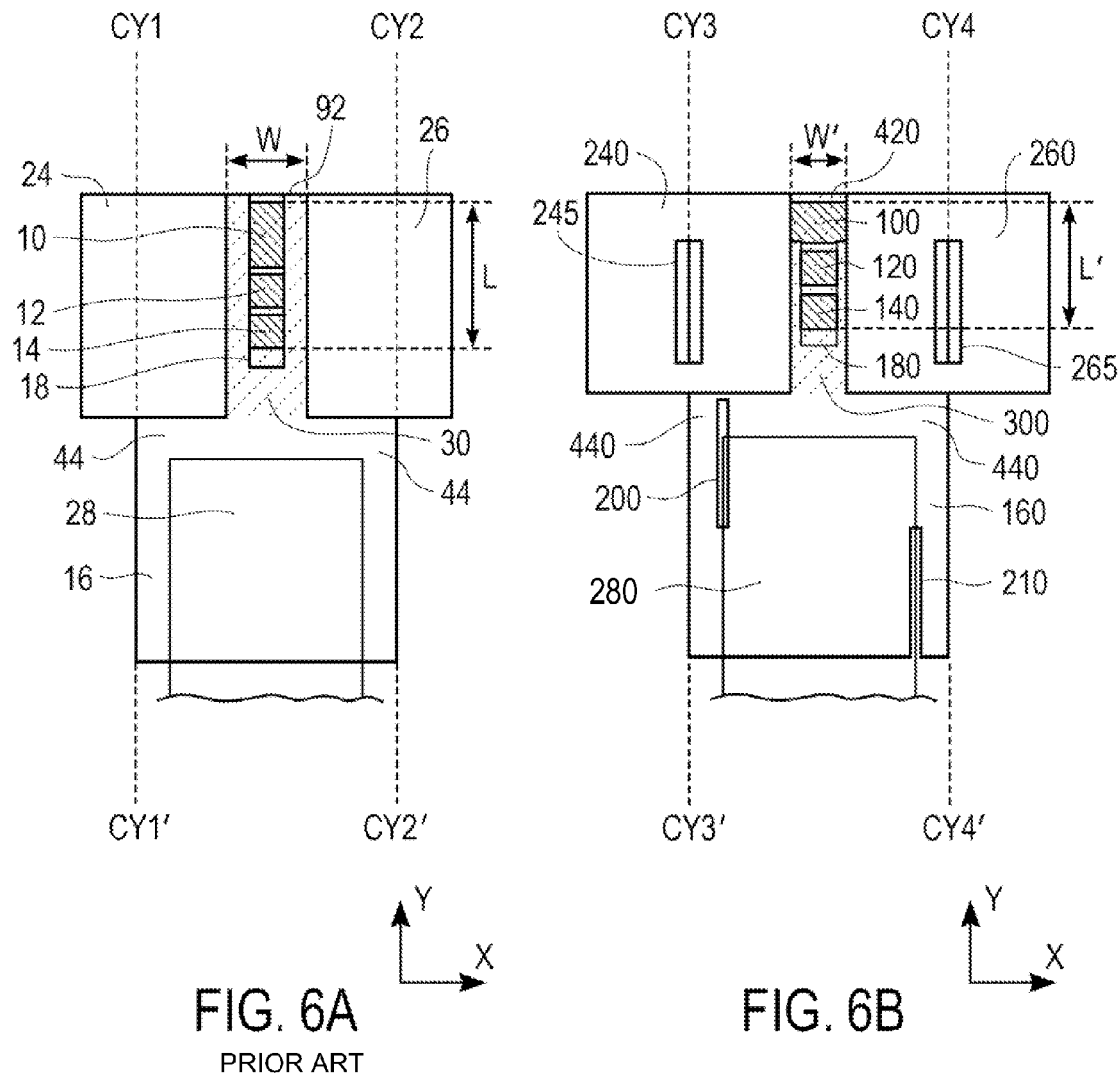
FIGS. 6A and 6B are a simplified partial top view of an adhesive layer disposed on the insulation layer and reagent layer of a respective test strip embodiment of the prior art and a reduced volume embodiment of the present invention.

FIGS. 6A and 6B shows a simplified partial top view of a test strip embodiment and reduced volume test strip embodiment indicating the fluidic pathway of the sample receiving chamber. The test strips in FIGS. 5A and 5B may be cut along incision line CX1-CX1' and CX2-CX2', respectively to create sample inlet (92 and 420) as shown in FIGS. 6A and 6B. The test strips in FIGS. 6A and 6B both have two vents (44 and 440) along both side edges of the strip which allows air to escape enabling fluid to wick into the sample receiving chamber.

A sample receiving chamber 300 as shown in FIG. 6B has a reduced volume because of its decreased sample receiving chamber length and width (L' and W') compared to the sample receiving chamber 30 as shown in FIG. 6A. In order to decrease the sample receiving chamber length, reference electrode 100 was increased in width and decreased in length allowing reference electrode 100 to have a sufficiently large area and more efficiently occupy the space within sample receiving chamber 300 such that the ratio of reference/working electrode area is about 2:1. An insulating layer 160 having a T-shaped aperture 180 was used to help expose a larger distal T-width TX1 of reference electrode 100 while exposing a narrower proximal T-width TX2 of working electrodes (120 and 140). Because distal T-width TX1 is larger than sample receiving chamber width W', the side edges of reference electrode 100 which may be wetted by liquid is defined by walls of the sample receiving chamber. In contrast, the width of the working electrodes (120 and 140) which may be wetted by liquid is defined by proximal T-width TX2 within T-shaped aperture 180. By using both insulation layer 160 and the adhesive layer to define the widths (along the X-axis) of the working electrodes (120 and 140) and reference electrode (100), a reduced volume strip can be more easily manufactured because of its simple alignment between the respective conductive layer, insulation layer 160, and adhesive layer. An alternative embodiment of a reduced volume strip may entail having a T-shaped aperture within the insulation layer and the adhesive layer. This would be much more difficult to manufacture due to alignment issues. In addition, a T-shaped aperture in the adhesive layer would create sharp edges within the sample receiving chamber which could negatively impact the capillary fluidics. In general, it is more desirable to have a smooth structure within a sample receiving chamber to create a uniform sample fill rate such as those illustrated in FIGS. 6A and 6B.

It will be recognized that equivalent structures may be substituted for the structures illustrated and described herein and that the described embodiment of the invention is not the only structure which may be employed to implement the claimed invention. In addition, it should be understood that every structure described above has a function and such structure can be referred to as a means for performing that function.

While preferred embodiments of the present invention have been shown and described herein, it will be obvious to those skilled in the art that such embodiments are provided by way of example only. Numerous variations, changes, and substitutions will now occur to those skilled in the art without departing from the invention.

It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An electrochemical glucose sensor comprising:
    a base substrate;
    a conductive layer disposed on said base substrate, and wherein said conductive layer comprises a reference electrode and at least two working electrodes;
    an insulation layer disposed on at least a part of said conductive layer such that the insulation layer is in contact with each of the two working electrodes to define spaced apart edges of an area which can be wetted by a liquid sample;
    a reagent layer disposed on said working electrodes and on at least a part of said reference electrode;
    an adhesive layer disposed on a portion of said reagent layer and conductive layer such that said adhesive layer is in contact with said portion to define spaced apart edges of an area over said reference electrode and reagent layer which can be wetted by a liquid sample.

2. An electrochemical glucose sensor of claim 1 further comprising:
    a hydrophilic layer disposed on said adhesive layer to form a sample receiving chamber, whereby a liquid sample can wick into said sample receiving chamber.

3. An electrochemical glucose sensor of claim 1, wherein said insulation layer further comprises:
    a T-shaped aperture having a proximal rectangle and a distal rectangle;
    wherein said proximal rectangle has a width and is contiguous with said distal rectangle which also has a width;
    said proximal rectangle substantially overlapping with said reference electrode;
    said distal rectangle substantially overlapping with said working electrodes; and
    said width of said proximal rectangle is greater than said width of said distal rectangle.

4. The electrochemical glucose sensor of claim 1, wherein said insulation layer comprises at least one registration guide so that said registration guide facilitates the alignment of said adhesive layer being disposed on said insulation layer.

5. The electrochemical glucose sensor of claim 4 wherein said registration guide further comprises a rectangular aperture within said insulation layer.

6. The electrochemical glucose sensor of claim 1, wherein said adhesive layer comprises at least one singulation guide so that said singulation guide facilitates the singulation of said electrochemical glucose sensor by reducing the amount of adhesive build up during singulation of the adhesive layer.

7. An electrochemical sensor comprising:
    a substrate;
    a reference electrode disposed on the substrate;
    at least one working electrode disposed on the substrate proximate the reference electrode;
    an insulation member disposed over the reference electrode and at least one working electrode, the insulation member having a aperture so that a portion of each the reference electrode and the at least one working electrode are exposed to receive a reagent, the aperture being in contact with the at least one working electrode to define a working electrode width as measured between two spaced apart edges of the aperture;
    a reagent layer disposed over the portion of each of the reference electrode and the at least one working electrode to define a coated area of the reference electrode and a coated area of the at least one working electrode; and an adhesive layer disposed over a portion of the insulation layer and over a portion of the coated area of the reference electrode to define a reference electrode width as measured between two spaced apart edges of the adhesive layer such that the reference electrode width as measured between the spaced apart edges of the adhesive layer is greater than the working electrode width as measured between the spaced apart edges of the aperture.

8. The electrochemical sensor of claim 7, in which the coated area of the reference electrode comprises an area of about 2 times the coated area of the at least one working electrode.

9. The electrochemical sensor of claim 7, in which the adhesive layer contacts the reagent layer.

* * * * *